(12) United States Patent
Medina et al.

(10) Patent No.: US 10,918,743 B2
(45) Date of Patent: Feb. 16, 2021

(54) CONTRAST MEDIUM FORMULATION AND RELATED PREPARATION METHOD

(71) Applicant: GUERBET, Villepinte (FR)

(72) Inventors: Christelle Medina, Vaires sur Marne (FR); Monique Sabatou, Rosny-sous-Bois (FR); Anne Petit, Leves (FR); Marc Port, Deuil la Barre (FR)

(73) Assignee: GUERBET, Villepinte (FR)

(*) Notice: Subject to any disclaimer, the term of this patent is extended or adjusted under 35 U.S.C. 154(b) by 586 days.

(21) Appl. No.: 14/786,926

(22) PCT Filed: Apr. 28, 2014

(86) PCT No.: PCT/EP2014/058617
§ 371 (c)(1),
(2) Date: Oct. 23, 2015

(87) PCT Pub. No.: WO2014/174120
PCT Pub. Date: Oct. 30, 2014

(65) Prior Publication Data
US 2016/0101196 A1    Apr. 14, 2016

(30) Foreign Application Priority Data

Apr. 26, 2013 (FR) .................... 13 53883

(51) Int. Cl.
| A61B 5/055 | (2006.01) |
| A61K 49/10 | (2006.01) |
| A61K 33/24 | (2019.01) |
| A61K 9/00 | (2006.01) |
| A61K 33/06 | (2006.01) |

(52) U.S. Cl.
CPC .......... A61K 49/108 (2013.01); A61K 9/0009 (2013.01); A61K 9/0019 (2013.01); A61K 33/06 (2013.01); A61K 33/24 (2013.01); A61K 49/106 (2013.01)

(58) Field of Classification Search
None
See application file for complete search history.

(56) References Cited

U.S. PATENT DOCUMENTS

| 4,647,447 | A | 3/1987 | Gries et al. |
| 5,403,572 | A | 4/1995 | Gries et al. |
| 5,582,814 | A | 12/1996 | Scott et al. |
| 5,595,725 | A | 1/1997 | Gries et al. |
| 5,876,695 | A | 3/1999 | Gries et al. |
| 5,876,698 | A | 3/1999 | Schmitt-Willich et al. |
| 6,440,956 | B1 | 8/2002 | Port |
| 6,559,330 | B1 | 5/2003 | Platzek et al. |
| 7,385,041 | B2 * | 6/2008 | Chang ................ A61K 49/0002 424/9.1 |
| 2003/0206858 | A1 | 11/2003 | Gries et al. |
| 2004/0170566 | A1 | 9/2004 | Chang et al. |
| 2006/0165591 | A1 | 7/2006 | Gries et al. |
| 2009/0169479 | A1 | 7/2009 | Port |
| 2009/0208421 | A1 * | 8/2009 | Meyer ................ A61K 49/106 424/9.361 |

FOREIGN PATENT DOCUMENTS

| CA | 2034242 A1 | 7/1991 |
| EP | 0463644 B1 | 6/1996 |
| EP | 0438206 B1 | 8/1996 |
| EP | 0454078 B1 | 10/1996 |
| EP | 1931673 B1 | 8/2012 |
| EP | 2 554 167 A1 | 2/2013 |
| FR | 2 891 830 A1 | 4/2007 |
| FR | 2 927 539 A1 | 8/2009 |
| WO | WO 89/00052 A1 | 1/1989 |
| WO | WO 93/11800 A1 | 6/1993 |
| WO | WO 98/48844 A2 | 11/1998 |
| WO | WO 2009/103744 A2 | 8/2009 |
| WO | WO 2011/073371 A1 | 6/2011 |

OTHER PUBLICATIONS

Toth et al. (Inorg. Chim. Acta 1996, 249, 191-199).*
International Search Report for PCT/EP2014/058617, dated Jul. 2, 2014.

* cited by examiner

*Primary Examiner* — Michael G. Hartley
*Assistant Examiner* — Melissa J Perreira
(74) *Attorney, Agent, or Firm* — Birch, Stewart, Kolasch & Birch, LLP

(57) ABSTRACT

The present invention relates to a liquid pharmaceutical composition including a complex of formula (I), in which M is an ion of a paramagnetic metal and R1 to R3, X1 to X3 and K1 to K12 are such as defined in claim 1, said composition also including a calcium complex of 1,4,7,10-tetraaza-cyclododecane-1,4,7,10-tetraacetic acid. The invention also relates to the preparation method thereof and to an imaging method involving said composition.

17 Claims, No Drawings

CONTRAST MEDIUM FORMULATION AND RELATED PREPARATION METHOD

The invention relates to formulations of contrast agents, in particular of paramagnetic metal ion chelates, in particular for magnetic resonance imaging, and to industrially effective processes for obtaining these formulations.

Numerous contrast agents based on lanthanide (paramagnetic metal) chelates, in particular gadolinium chelates, described for example in document U.S. Pat. No. 4,647,447, are known. These products are often grouped together under the term GBCA (Gadolinium-based Contrast Agent). Several products are commercially available, in particular based on macrocyclic chelates, such as gadoterate DOTA (1,4,7,10-tetraazacyclododecane-N,N',N'',N'''-tetraacetic acid), gadoteridol HPDO3A and gadobutrol DO3A-butrol, and linear chelates such as DTPA (diethylenetriaminepentaacetic acid), DTPA-BMA (gadodiamide) or BOPTA (gadobemate). These compounds will, in the remainder of the text, be referred to without distinction as "chelates" or "chelating ligands".

Other products, some of which are undergoing development, represent a new generation of GBCAs. Mention may in particular be made of complexes of macrocyclic chelates such as bicyclopolyazamacrocyclocarboxylic acid (EP 0 438 206) or of macrocyclic chelates derived from PCTA (i.e. comprising at least the chemical structure of 3,6,9,15-tetraazabicyclo[9,3,1]pentadeca-1(15),11,13-triene-3,6,9-triacetic acid), as described in documents WO 93/11800, U.S. Pat. Nos. 5,403,572, 6,440,956 or EP 1 931 673.

The PCTA-derived chelating-ligand complexes described in document EP 1 931 673 have in particular the advantage of being relatively easy to chemically synthesize and of having a relaxivity greater than the other GBCAs (relaxivity $r_1$ which can range up to 11-12 $mM^{-1} \cdot s^{-1}$ in water) currently on the market, this relaxivity corresponding to the effectiveness of these products and therefore to their contrasting power.

Lanthanide chelates are in a situation of chemical equilibrium. There is therefore a risk of unwanted release of paramagnetic metal. Those skilled in the art are thus led to search for technical solutions which limit this risk in order to completely safely solve the complex technical problem of tolerance in the patient, in particular when the paramagnetic metal is gadolinium. This problem is all the more tricky since the administration of contrast agents is often repeated during diagnostic examinations and/or for guiding and monitoring the effectiveness of a therapeutic treatment.

The complex problem of the tolerance of new GBCAs must always be considered, in particular in situations where there is a more pronounced tolerance risk for the administration of MRI contrast products. Since 2006, a pathological condition known as NSF (Nephrogenic Systemic Fibrosis) has been at least partly linked to the existence of gadolinium in the body. This disease has resulted in a warning by health authorities with respect to gadolinium-containing contrast agents sold for certain categories of patients.

In fact, this technical problem of lanthanide chelate tolerance remains complex and considerable.

A first strategy for limiting this risk is to select complexes which have the highest possible thermodynamic and kinetic stabilities. This is because the higher the stabilities of the complex, the more limited the amount of lanthanide released over time will be.

Several other lines for improving gadolinium chelate tolerance are described in the prior art. The document U.S. Pat. No. 5,876,695 discloses formulations comprising an excess of free chelate, intended to compensate for an unwanted release of the lanthanide, the excess chelate complexing the lanthanide (for example the gadolinium) released. Document U.S. Pat. No. 5,876,695 describes in particular an excess of linear chelate, in particular of free DTPA. This formulation strategy is used for products such as Magnevist®, Vasovist® or Primovist®. Document WO 2009/103744 describes a similar formulation strategy, based on the addition of a precise amount of free chelate, so as to have a very small excess of said chelate and a zero concentration of free lanthanide.

Documents EP 0 454 078, U.S. Pat. No. 5,876,695 and US 2004/0170566 describe the use of "weak" complexes of a macrocyclic or linear ligand with a metal or an alkaline-earth metal, in particular calcium, sodium, zinc or magnesium. These "weak" complexes undergo transmetallation in the presence of free lanthanide, since the complexes between said macrocyclic or linear ligands and a lanthanide, in particular gadolinium, are "stronger", i.e. they are more thermodynamically stable. An exchange therefore takes place between the calcium, sodium, zinc or magnesium and the lanthanide: the latter is trapped by the ligand in complex form, while the calcium, sodium, zinc or magnesium is released into the solution. This formulation strategy is, itself, used for products such as Gadovist®, Omniscan® or Opti-Mark®. It should be noted that, in the examples of these documents, the ligand of the "weak" complex is identical to the ligand of the active gadolinium complex (i.e. used as contrast product). These documents mention the possibility of using two different ligands, provided, however, that the stability constant of the "weak" complex is lower than that of the active gadolinium complex (see in particular U.S. Pat. No. 5,876,695, column 4, lines 52-58).

The applicant has carried out numerous studies on the specific case of macrocyclic chelates and in particular of the PCTA-derived chelates as described in EP 1 931 673. It has attempted to apply the various known solutions in terms of formulation, but said solutions have proven to be impossible to implement or to be economically nonprofitable in the precise case of complexes between these PCTA-derived chelates and paramagnetic metal ions, or unsatisfactory in terms of ensuring that paramagnetic metal ions such as gadolinium are not released, both during the process for producing the contrast product and during the storage of this product, before it is used in a patient. An important element to be taken into account is the fact that these complexes, while having a very high kinetic stability, have a low thermodynamic constant.

The Applicant has already not wanted to use linear chelating ligands since these chelates are not sufficiently stable to ensure an absence of release of paramagnetic metal ions during the life of the GBCA. Subsequently, the Applicant has been surprised to note that the use of macrocyclic chelates having chemical structures close to that of the chelate also do not make it possible to ensure this absence of paramagnetic metal ions in the formulation. Using the formulations already existing on the market or the teaching of prior art documents as a basis, a person skilled in the art would be strongly prompted to use, for the formulation of paramagnetic metal chelate complexes, only the ligand of these complexes that is free or complexed with calcium.

For a person skilled in the art, the use of a chelating ligand that is free or in the form of a complex of a metal or of an alkaline-earth metal such as calcium, that would have a thermodynamic stability greater than that of the complex to be formulated is not desirable since there would be the risk of an exchange of paramagnetic metal in favor of the chelate having a higher thermodynamic constant for the paramagnetic metal.

It is by overcoming this technical prejudice that the Applicant has been able to provide a solution to the technical problem of the tolerance of PCTA-derived paramagnetic metal chelates.

The Applicant has been able to demonstrate that macrocyclic chelates, and more especially DOTA, have a behavior that is different than linear chelates such as DTPA in terms of tolerance resulting from excess ligand. However, for the reasons explained above, a person skilled in the art would have been dissuaded from using DOTA for preparing a composition comprising a PCTA-derived complex.

Indeed, the applicant has discovered that the addition of DOTA (1,4,7,10-tetraazacyclododecane-1,4,7,10-tetraacetic acid) salts to a composition comprising a paramagnetic metal complex of a PCTA derivative makes it possible to ensure the absence of release of paramagnetic metal in the formulation, in particular in the injectable solution, as well as in the patient's body after injection, while preserving the performance levels as contrast product in medical imaging.

A subject of the present invention therefore relates to a liquid pharmaceutical composition comprising a PCTA-derived complex and also comprising a calcium complex of 1,4,7,10-tetraazacyclododecane-1,4,7,10-tetraacetic acid, preferentially a monocalcium complex of 1,4,7,10-tetraazacyclododecane-1,4,7,10-tetraacetic acid (DOTA-Ca) or a dicalcium complex of 1,4,7,10-tetraazacyclododecane-1,4,7,10-tetraacetic acid (DOTA-Ca$_2$), and having a concentration of free paramagnetic metal of less than 1 ppm (w/v), preferentially less than 0.5 ppm (w/v).

In the remainder of the text, an alternative way of denoting a complex between a chelating ligand of formula (I) and a paramagnetic metal will be to refer to it as "PCTA— paramagnetic metal". For example, unless otherwise indicated, the complex between this chelating ligand of formula (I) and a gadolinium ion will be denoted by "PCTA-Gd". A complex between DOTA and gadolinium will be denoted by "DOTA-Gd".

Another subject of the invention relates to a contrast product for medical imaging comprising said composition.

Another subject of the present invention relates to a process for preparing said composition.

The present invention also relates to said composition or said contrast product for use thereof in a diagnostic method.

Thus, the invention relates to a liquid pharmaceutical composition comprising a complex of formula (I):

(I)

[Chemical structure diagram]

in which $R_1$, $R_2$ and $R_3$ represent —COOH,
$X_1$, $X_2$ and $X_3$ represent, independently of one another, L-Y in which L represents a $C_1$-$C_3$ alkylene group, preferably (CH$_2$), with n=1 to 3, and Y represents —CONH$_2$, —CO—NR$_7$R$_8$ or —NR$_7$—CO—R$_8$, in which R$_7$ represents H or a $C_1$-$C_6$ alkyl group or a $C_1$-$C_6$ hydroxyalkyl group, which is in particular $C_2$-$C_4$, advantageously —CH$_2$—CH$_2$OH, —CHOH—CH$_2$OH, —CH—(CH$_2$OH)$_2$, —(CH$_2$)$_m$— (CHOH)$_p$—CH$_2$OH with m=1 to 3, p=1 to 4 and m+p=2 to 5 or —C—(CH$_2$OH)$_3$ and R$_8$ represents a $C_1$-$C_6$ alkyl or $C_1$-$C_6$ hydroxyalkyl group, which is in particular $C_2$-$C_4$, advantageously —CH$_2$—CH$_2$OH, —CHOH—CH$_2$OH, —CH—(CH$_2$OH)$_2$, —(CH$_2$)$_m$—(CHOH)—CH$_2$OH with m=1 to 3, p=1 to 4 and m+p=2 to 5 or —C—(CH$_2$OH)$_3$, provided that at least R$_7$ or R$_8$ represents a $C_1$-$C_6$ hydroxyalkyl group;

D represents CH or N;
E represents CH or N;
F$_1$ represents CH or N;
K$_1$ to K$_{12}$ each independently represent H, —(CH$_2$)$_j$—CH$_3$ or —(CH$_2$)$_i$—OH in which j=0 to 3 and i=1 to 3, advantageously H, or K$_3$ or K$_4$ with K$_5$ or K$_6$, and/or K$_7$ or K$_8$ with K$_9$ or K$_{10}$ forming a ring having 3 to 6 carbon atoms; and
M represents an ion of a paramagnetic metal;
or an enantiomer or a diastereoisomer (preferentially chosen from the diastereoisomers RRS, RSR and RSS) thereof or mixtures thereof, said composition also comprising a calcium complex of 1,4,7,10-tetraazacyclododecane-1,4,7,10-tetraacetic acid, preferentially a monocalcium complex of 1,4,7,10-tetraazacyclododecane-1,4,7,10-tetraacetic acid (DOTA-Ca) or a dicalcium complex of 1,4,7,10-tetraazacyclododecane-1,4,7,10-tetraacetic acid (DOTA-Ca$_2$), and having a concentration of free paramagnetic metal of less than 1 ppm (m/v), preferentially less than 0.5 ppm (m/v).

Preferentially, the calcium complex of 1,4,7,10-tetraazacyclododecane-1,4,7,10-tetraacetic acid according to the invention will be a monocalcium complex of 1,4,7,10-tetraazacyclododecane-1,4,7,10-tetraacetic acid.

For the purposes of the present invention, the term "alkyl group" or "alkylene group" is intended to mean any straight or branched unsubstituted chain of carbon atoms (preferably 1 to 5) and the term "hydroxyalkyl group" is intended to mean any alkyl chain as defined above comprising one or more hydroxyl groups. It is recalled that the term "$C_1$-$C_n$" is intended to mean any group comprising from 1 to n carbon atoms. Thus, the term "$C_1$-$C_6$ alkyl group" is intended to mean in particular a group chosen from methyl, ethyl, n-propyl, i-propyl, n-butyl, i-butyl, t-butyl, pentyl and hexyl. In addition, the term "$C_1$-$C_6$ alkylene group" is intended to mean in particular a group chosen from methylene, ethylene, n-propylene, i-propylene, n-butylene, i-butylene, t-butylene, pentylene and hexylene.

Subsequently, the calcium complex of 1,4,7,10-tetraazacyclododecane-1,4,7,10-tetraacetic acid will be denoted DOTA-calcium or DOTA-Ca whether it is the monocalcium complex or the dicalcium complex.

The composition according to the invention has the advantage of exhibiting a nonexistent risk, before the expiry date, of unwanted release of paramagnetic metal, this being by virtue of the choice of specific formulation of the complex of formula (I) as previously defined as a mixture with the DOTA-calcium complex.

The composition according to the invention thus exhibits stability over time, that is to say its composition remains in accordance with the specifications in terms of concentration of free paramagnetic metal (in particular its concentration of free paramagnetic metal remains less than 1 ppm (m/v)), over a period of at least three years, preferentially of at least four years or more preferentially of at least five years, in particular in terms of content of free paramagnetic metal.

According to the ICH guidelines, observation of this stability for six months at 40° C. is considered to be a good indication of stability for three years at 25° C.

Complex of Formula (I)

Particular preference is given to the complexes of formula (I) for which the three Y chains each have a molecular weight of less than 200, advantageously between 50 and 100, and in particular the compounds for which the Y chains each comprise 1 to 5 OH groups. The invention also covers a composition comprising one of the complexes of formula (I) for which m+p>5, i.e. resulting from each of the possible combinations between m=1, 2, 3 and p=1, 2, 3, 4, in particular m=2 and p=4, m=3 and p=4, or m=3 and p=3.

According to advantageous implementations, the complex of formula (I) is such that E represents an N atom and D and $F_1$ represent CH.

According to advantageous embodiments, the complex of formula (I) is such that $X_1$ to $X_3$ independently represent —$(CH_2)_n$—CO—$NR_7R_8$ or —$(CH_2)_n$—$NR_7$—CO—$R_8$, in which n is between 1 and 3, $R_7$ represents H or a methyl group, and $R_8$ represents a $C_1$-$C_6$ hydroxyalkyl group, which is advantageously $C_2$-$C_3$, preferably —$CH_2$—$CH_2OH$, —CHOH—$CH_2OH$, —CH—$(CH_2OH)_2$, —$CH_2$—$(CHOH)_p$—$CH_2OH$ with p=1 to 4 or —C—$(CH_2OH)_3$.

Advantageously, $X_1$ to $X_3$ independently represent —$(CH_2)_n$—$CONR_7R_8$ in which n is between 1 and 3, $R_7$ represents H or a methyl group, and $R_8$ represents a $C_1$-$C_4$ hydroxyalkyl group, preferably —$CH_2$—$CH_2OH$, —$CHOHCH_2OH$, —CH—$(CH_2OH)_2$, —$CH_2$—$(CHOH)_p$—$CH_2OH$ with p=1 or 2 or —C—$(CH_2OH)_3$.

Advantageously, $X_1$ to $X_3$ independently represent —$(CH_2)_n$—$CONR_7R_8$, in which n is between 1 and 3, $R_7$ represents H, and $R_8$ represents —$CH_2$—$CH_2OH$, —CHOH—$CH_2OH$, —CH—$(CH_2OH)_2$, —$CH_2$—$(CHOH)$ p-$CH_2OH$ with p=1 to 4 or —C—$(CH_2OH)_3$.

Preferentially, the complex of formula (I) is chosen from the complexes between a ligand of formulae (I') and (I"):

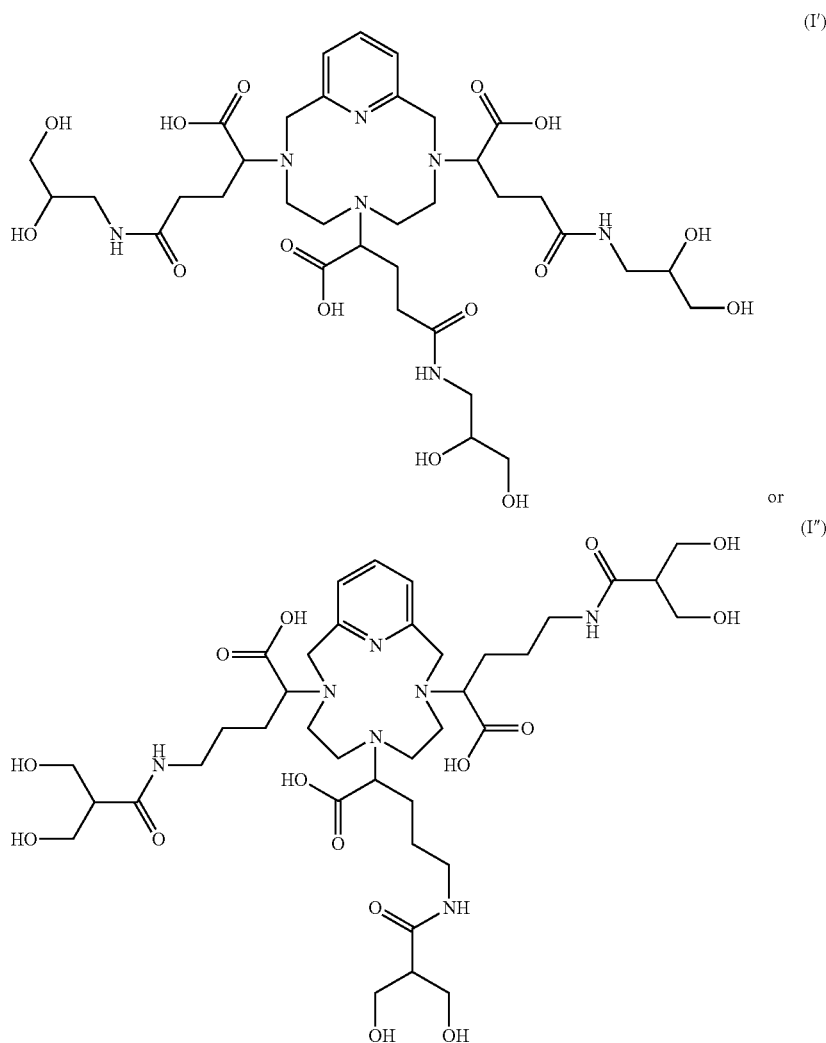

and a paramagnetic metal ion M.

Advantageously, the paramagnetic metal ion M is chosen from the ions of a paramagnetic metal having an atomic number of 21-29, 42-44 or 58-70, i.e. scandium (Sc), titanium (Ti), vanadium (V), chromium (Cr), manganese (Mn), iron (Fe), cobalt (Co), nickel (Ni) or copper (Cu) ions or molybdenum (Mo), technetium (Tc) or ruthenium (Ru) ions or cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm) or ytterbium (Yb) ions. The paramagnetic metal ion M is preferentially chosen from manganese, iron and lanthanide ions, more preferentially chosen from the ions $Mn^{2+}$ and $Fe^{3+}$ and gadolinium ions, for instance $Gd^{3+}$ and even more preferentially chosen from lanthanide ions and in particular gadolinium ions, for instance $Gd^{3+}$.

The complexes of formula (I) as previously defined have a relaxivity (efficiency in imaging) and a mass efficiency (industrial cost price) which are very markedly improved, with in particular relaxivity values r1 of the order of 9 to 15 $mM \cdot s^{-1} \cdot Gd^{-1}$, i.e. relaxivity values multiplied by a factor of 2 to 3 with respect to those of the prior derivatives in particular of DO3A, DOTA and DTPA. These compounds are very suitable for high magnetic field imaging (for example for fields of 3 Tesla). The complexes of formula (I) exhibit several functional characteristics which are particularly outstanding once combined:

1. non-ionicity: this makes it possible to greatly limit the osmolality of the product to be injected and thus the dose of product injected, which is an important characteristic for contrast products in order to improve patient comfort and to reduce the cost of the injection;

2. high hydrophilicity: this enables non-toxicity and appropriate solubility of the product;

3. high relaxivity (high intensity of the signal): the relaxivity is high and is not detrimentally affected (unquenched) by the hydroxyl groups of the structure;

4. low industrial cost price (high mass efficiency); and 5. low molecular weight making it possible to obtain a nonspecific compound biodistribution: for example, undesired behavior of blood pool agent type, which corresponds to selective diffusion in the vascular compartment in particular, is avoided.

The processes for synthesizing these complexes of formula (I) are well known to those skilled in the art, and are in particular described in document EP 1 931 673.

In the particular case where M represents a gadolinium ion, for the following chemical equilibria:

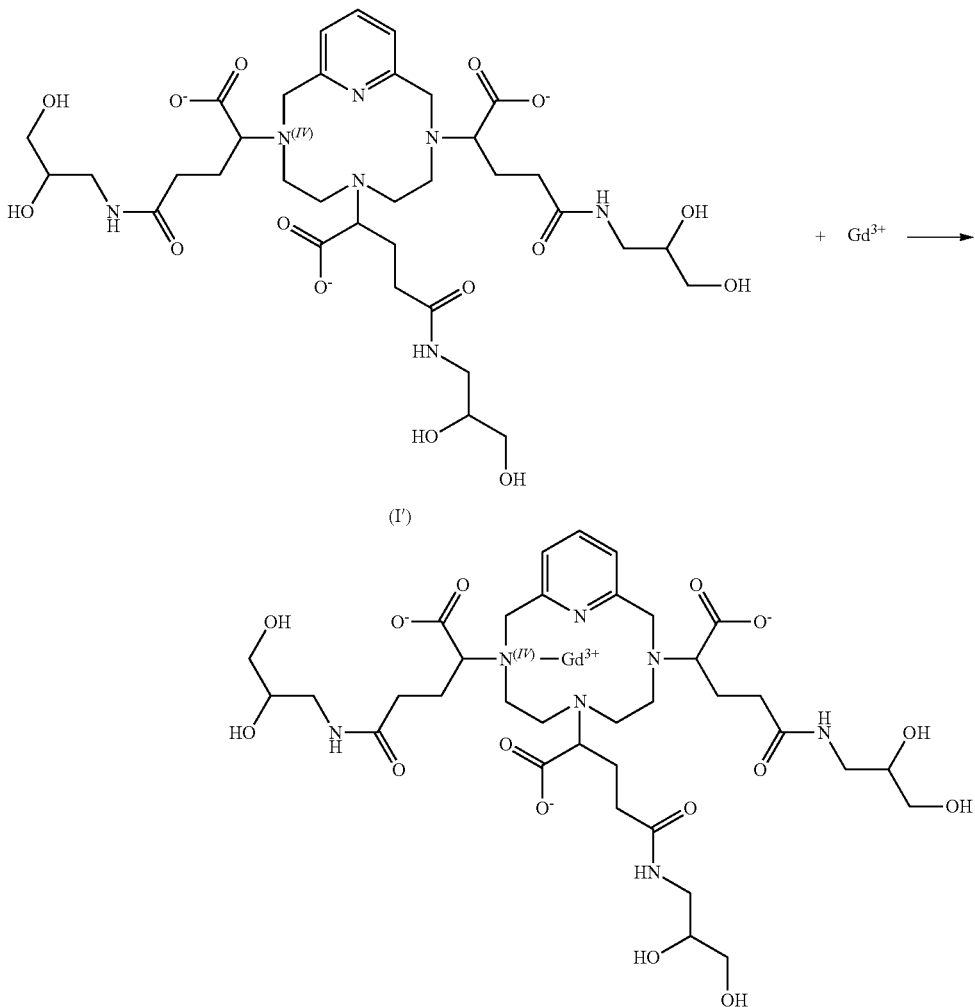

(equation 1)

and

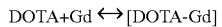   (equation 2)

the thermodynamic equilibrium constant of equation 1 (i.e. for the complexation of $Gd^{3+}$ by the ligand of formula I') is $10^{14.9}$ (i.e. log (Ktherm)=14.9), while the thermodynamic equilibrium constant of equation 2 (i.e. for the complexation of $Gd^{3+}$ by DOTA) is $10^{25.6}$ (i.e. log (Ktherm)=25.6). Thus, the formulations according to the invention go against the teachings of document U.S. Pat. No. 5,876,695 in particular, since the complex of DOTA with the gadolinium ion is more thermodynamically stable than the active complex.

PREFERRED EMBODIMENTS

In particular, the composition according to the invention has a concentration of complex of formula (I) described above comprised between 0.001 and 1.5 mol·l$^{-1}$, preferentially between 0.2 and 0.7 mol·l$^{-1}$, more preferentially between 0.3 and 0.6 mol·l$^{-}$.

The complex of formula (I) is assayed by methods known to those skilled in the art. It can in particular be assayed after mineralization and assaying of the total paramagnetic metal present in the composition. In the case of the assaying of the total gadolinium present in the solution, the assaying is carried out by optical emission spectrometry (also called ICP-AES or ICP Atomic Emission Spectrometry).

The content of complex of formula (I) allows this composition to have an optimal contrasting power while having a satisfactory viscosity. Indeed, below 0.01 mol·l$^{-1}$ of complex of formula (I) described above, the performance levels as contrast product are less satisfactory, and at a concentration above 1.5 mol·l$^{-1}$, the viscosity of this composition becomes too great for easier handling.

In one advantageous embodiment, the proportion of the DOTA-calcium complex is from 0.002% to 5% mol/mol, for example from 0.002% to 1% mol/mol, preferentially from 0.01% to 5%, more preferentially from 0.25% to 5% or from 0.01% to 0.5% mol/mol, even more preferentially from 0.25% to 0.5% mol/mol, this proportion being related to the proportion of complex of formula (I) in said composition.

The DOTA-calcium complex is also assayed by methods known to those skilled in the art, for example by HPLC (for example by ion-pair HPLC: using a liquid-phase chromatograph equipped with a diode array detector (detection carried out by UV at 205 nm) and with a C18 column; the solvent used is methanol (Prolabo)).

Preferentially, the proportions specified in the present invention and in particular above are proportions before sterilization of the composition.

Advantageously, the pH of the composition is between 4.5 and 8.5, preferentially between 5 and 6.5. These pH ranges make it possible in particular to limit the appearance of certain impurities and to favor the complexation of the paramagnetic metal ion M. In particular, the composition according to the invention can be buffered, i.e. it can also comprise a buffer chosen from standard buffers established for the pH range 5 to 6.5 and preferentially chosen from lactate, tartrate, malate, maleate, succinate, ascorbate, carbonate, Tris (Tris(hydroxymethyl)aminomethane), HEPES (2-[4-(2-hydroxyethyl)-1-piperazine]ethanesulfonic acid), and MES (2-morpholinoethanesulfonic acid) buffers and mixtures thereof, and preferentially a buffer chosen from lactate, tartrate, carbonate, and MES buffers and mixtures thereof.

Owing in particular to the trapping of the free paramagnetic metal by DOTA, the composition which is the subject of the invention may also comprise a complex between DOTA and a metal, preferentially in a proportion of from 0.002% to 0.5% mol/mol, preferentially from 0.01% to 0.5% mol/mol, this proportion being related back to the proportion of complex of formula (I) in said composition. Preferentially, the complex between DOTA and a paramagnetic metal is a complex between DOTA and a gadolinium ion (in particular Gd$^{3+}$). The nature of the metal chelated by DOTA is predominantly the same as that of the paramagnetic metal chelated by the ligand of the complex of formula (I). However, the composition according to the invention can also comprise a small proportion of complex between DOTA and a metal other than the one chelated by the ligand of the complex of formula (I). The composition can thus also comprise a complex between DOTA and an ion of any metal that can be extracted from the containers in which the composition is prepared and/or stored, in particular an iron, copper and/or magnesium ion.

The complex between a chelating ligand and a lanthanide is preferentially chosen from the complexes of formula (I) for which M represents a lanthanide ion, and more preferentially from the complexes of formula:

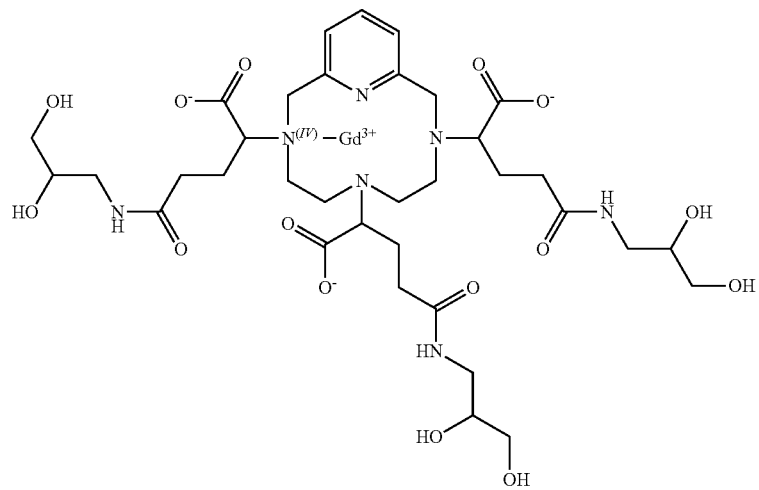

or

-continued

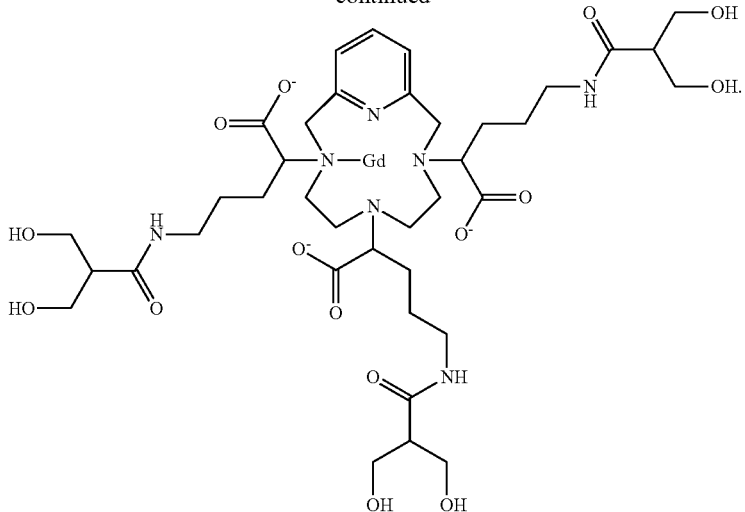

The composition which is the subject of the invention is preferentially sterile.

Process for Preparing a Pharmaceutical Composition in Accordance with the Invention The present invention also relates to a process for preparing a composition according to the invention. Indeed, the paramagnetic metals released during the formulation of these complexes and/or during the storage of contrast products comprising these complexes originate predominantly from the aging during storage of the chelates; it has been possible to provide a technical solution in order to enable extremely rapid trapping of the lanthanides released.

Thus, according to the invention, the process for preparing the liquid pharmaceutical composition described above comprises the following successive steps:
a) dissolution of the complex of formula (I) as previously defined, in a pharmaceutically acceptable medium,
b) addition, to the solution obtained at the end of step a), of an amount of free DOTA comprised between 0.002% and 5% mol/mol relative to the amount of complex of formula (I) present in the composition, and,
c) addition, to the solution obtained at the end of step b), of 0.002% to 5% mol/mol of a calcium salt or of calcium oxide.

For the purposes of the present invention, the term "pharmaceutically acceptable medium" is intended to mean a medium that is compatible with intravenous injection. Preferentially, this medium is sterile water, or a sterile saline solution, preferably sterile water. This medium is preferentially buffered, i.e. it can also comprise a buffer chosen from standard buffers established for the pH range 5 to 6.5 and preferentially from lactate, tartrate, malate, maleate, succinate, ascorbate, carbonate, Tris, HEPES and MES buffers and mixtures thereof, and preferentially a buffer chosen from lactate, tartrate, carbonate and MES buffers and mixtures thereof.

For the purposes of the present invention, the term "free DOTA" is intended to mean that the DOTA ligand is present in a non-complexed form, in particular non-complexed with a paramagnetic metal, and is not added in the form of an excipient X[X', DOTA] where X and X' are a metal ion or alkaline-earth metal ion, in particular chosen independently from calcium, sodium, zinc and magnesium. In particular, the free DOTA is not in the form of a salt, in particular the free DOTA is not in the form of a calcium salt, such as DOTA-Ca (monocalcium salt), DOTA-Ca$_2$ (dicalcium salt) or DOTA-Ca—Na$_z$ (disodium calcium salt). An example of free DOTA is its tetraacid form (1,4,7,10-tetraazacyclodo-decane-1,4,7,10-tetraacetic acid).

Preferentially, the calcium salt is calcium chloride ($CaCl_2$).

Step a) of dissolution of the complex of formula (I) previously defined is preferentially carried out by heating the pharmaceutically acceptable medium to a temperature of at least 45° C., or even at least 60° C.

Steps b) of addition of free DOTA and/or c) of addition of a calcium salt are advantageously carried out, after a decrease in the temperature of the solution obtained in step a), at a temperature of 20 to 40° C. This temperature range is optimal for limiting gadolinium exchanges between the complex of formula (I) previously defined and the DOTA.

Adding DOTA not in the form of a salt but in free form makes it possible to make the complexation of the free paramagnetic metal (for example of a lanthanide such as gadolinium released from a Gd complex) more efficient. This paramagnetic metal is thus trapped more rapidly than if DOTA salts were used, as described in the prior art.

In one particularly advantageous embodiment, the amount (as mole percentage) of calcium salt or of calcium oxide added to the solution in step c) is identical to the amount of free DOTA added in step b).

Advantageously, the process according to the invention also comprises a step c') of adjustment of the pH of the solution obtained in step c), to a pH of from 4.5 to 8.5, preferentially from 5 to 6.5.

This step c') of adjustment of the pH is preferentially carried out by adding one of the buffers mentioned below and/or by adding a 0.1 N solution of sodium hydroxide NaOH or a 0.1 N solution of hydrochloric acid HCl.

Advantageously, the process according to the invention also comprises, after step c) or step c'), a step d) of adjustment of the concentration of said complex of said formula (I), after measurement of the density of the composition, by adding pharmaceutically acceptable medium. The target final concentration of complex of formula (I) in the composition is preferentially comprised between 0.001 and 1.5 mol·l$^{-1}$, more preferentially between 0.2 and 0.7 mol·l$^{-1}$ and even more preferentially between 0.3 and 0.6 mol·l$^{-1}$.

The step of adjustment of the concentration of the complex of formula (I) as previously defined is preferentially a step of adjustment of the volume by adding pharmaceutically acceptable medium so as to adjust the density of the liquid composition to a density preferentially comprised between 0.1 and 1.3 g·cm$^{-3}$, more preferentially from 1.0 to 1.3 g·cm$^{-3}$.

The process according to the invention can also comprise a step of measurement of the amount of DOTA and/or of paramagnetic metal in excess at the end of step a) and/or of step b) and/or of step c) and/or of step c'), and/or of step d).

These assays are carried out according to methods known to those skilled in the art. The assaying of gadolinium is, for example, carried out by colorimetry with Xylenol Orange. Xylenol Orange forms, with the free gadolinium, a colored complex having a specific absorbance at the wavelength $\lambda=567$ nm at pH=5.6.

A sterilization step, advantageously after step c), c') or d) of the process in accordance with the invention, can also advantageously be added to this process. This sterilization is carried out according to methods known to those skilled in the art. Preferentially, the composition is sterilized according to an overkill approach. This approach requires little information regarding the biocontaminants of the composition. With this approach, the most extreme case of biocontamination is applied and sterilization conditions which make it possible to obtain a PNSU (Probability of a Non-Sterile Unit) of 10$^{-6}$ for the composition thus sterilized are applied. Any sterilization process which shows that the Fbio and Fphy lethality indices (lethality calculated on the basis of physical parameters of the sterilization cycle—this is the integration of the lethal level (L) as time progresses) are greater than 12 minutes is suitable for implementing this overkill approach. An example of sterilization according to an overkill approach is a sterilization by wet heat at 121° C. for 15 minutes (Decision three for the selection of Sterilisation Methods, Annex to Note for Guidance on Development Pharmaceutics (CPMP/QWP/054/98 Corr), EMBA, April 2000). An Alphaklave® 23 autoclave (HMCE—France) can be used to carry out this sterilization.

Thus, in one preferred embodiment of the invention, the process comprises the successive steps a), b), c), c') and d), and also a sterilization step, said steps being as previously defined.

The concentration, in the composition, of complex of formula (I) is typically between 1 mM and 0.6 M. The dose administered to the patient is typically of the order of 0.01 to 5 mmol/Kg.

Use of the Compositions and Contrast Products According to the Invention

The invention also relates to the use of a composition according to the invention for preparing a diagnostic composition for medical imaging, or a composition for diagnostic monitoring of the efficacy of the therapeutic treatment, and a diagnostic method comprising the administration of a pharmaceutically acceptable amount of a pharmaceutical composition as described above. The invention thus relates to a contrast product for medical imaging, comprising such a liquid pharmaceutical composition.

The invention also relates to the compositions or the contrast products previously described, for use thereof in the diagnosis of diseases, in particular cancerous, inflammatory, neurodegenerative or vascular diseases, in particular of cardiovascular diseases.

The invention also relates to said compositions or said contrast product which were previously described, for the use thereof in an imaging method, in particular a method as described below.

Thus, the invention relates to a method for imaging the whole body or a part of the body of an individual, comprising a step of obtaining one or more images of the whole body or of a part of the body of an individual by means of a medical imaging technique, in which said whole body or said part of the body of the individual comprises the composition defined above or the contrast product defined above (preferably in an effective amount) and in which the image(s) is (are) associated with the magnetic particles based on an iron compound that are contained in the composition defined above or in the contrast product defined above.

According to one embodiment, the imaging method according to the invention does not include a step of injection or of invasive administration of the composition or of the contrast product to the individual.

According to another embodiment, the imaging method according to the invention comprises a prior step of injection or of administration of the composition or of the contrast product to the individual, preferably an intravascular injection.

In the methods defined above, the images are preferably obtained by Magnetic Resonance Imaging (or MRI).

The term "effective amount" is intended to mean an amount of composition according to the invention, or of a contrast product comprising this composition, which makes it possible to obtain the images by means of the medical imaging technique used.

For a diagnosis by MRI, the intravenous administration by injection, usually in saline solution, is typically carried out at a dose of 1 to 500 µmol Gd/kg. The pharmaceutically acceptable unit doses will depend on the route of administration, and also on the patient and in particular on the nature of the disorder to be studied.

For an intravenous injection and observation by magnetic resonance, the concentration of the solution is typically between 0.001 and 1 mol/liter, and the dose administered to the patient according to his or her weight will be, as appropriate, from 0.001 to 0.3 millimol/kilo.

Among the advantageous diagnostic indications, mention will be made of the indications already clinically used, and the indications for which the results are improved by virtue of the formulations. Mention will thus be made of the following indications and the improvements thereof: angiography, brain imaging (of the central nervous system in particular), vascular imaging, imaging of cardiovascular, cancerous, neurodegenerative or inflammatory diseases, any indication with perfusion imaging, any indication combining the use of several contrast products, in particular MRI, X-ray scan, SPECT scan, PET scan, PET CT scan, any indication with successive administrations of contrast products or in multimodal imaging.

According to particular embodiments, it can be chosen to administer the formulations according to the invention in combination with or in place of formulations of the prior art, depending on the patient's diagnostic profile, and in particular on the patient's profile of tolerance to contrast products.

The diagnostic compositions of the invention can also comprise additives such as antioxidants, buffers, osmolality regulators or stabilizers. Formulation examples appear in general handbooks and in particular in Remington's Pharmaceutical Sciences 18$^{th}$ Edition (1990), Mack. Pub. It is, for example, possible to prepare sterile aqueous or saline solutions comprising galenical adjuvants (lactose, methylcellulose, mannitol), and/or surfactants (lecithins, Tween® or similar products). Excipients such as, for example, mannitol may also be used. A pharmaceutically acceptable dose refers to a dose that is appropriate for therapeutic or diagnostic use.

The invention will be illustrated by means of the nonlimiting examples which follow.

DETAILED EXAMPLES

Example 1

Example of a Production Process in Accordance with the Invention

The process for producing a composition is carried out according to the following steps:

a) 485.1 g (i.e. 0.5 M) of complex between a chelating ligand of formula (I') and a gadolinium ion ($Gd^{3+}$), which is in the form of an odorless white powder, are dissolved in water (qs 1 liter) by heating the vessel to a temperature of 50° C. and stirring the solution vigorously until complete dissolution of this complex in the water. The solution is then cooled to approximately 30° C.

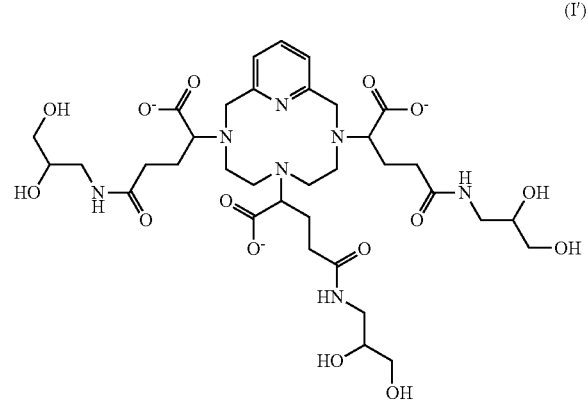 [SMILES: O=C(CCC(C(=O)[O-])N1CCN(C(CCC(=O)NCC(O)CO)C(=O)[O-])Cc2cccc(n2)CN(C(CCC(=O)NCC(O)CO)C(=O)[O-])CC1)NCC(O)CO]

(I')

b) 1.011 g (i.e. 0.5% mol/mol relative to the proportion of complex added in step a)) of DOTA (Simafex, France) are added to the solution obtained in step a).

c) 0.368 g (i.e. 0.5% mol/mol relative to the proportion of complex added in step a)) of calcium chloride ($CaCl_2$, $2H_2O$) (Merck) is added to the solution obtained in step b).

c') if required, the pH of the solution obtained in step c) is adjusted to a pH of 5 to 6 by decreasing, where appropriate, the pH by adding a 0.1N solution of hydrochloric acid or by increasing, where appropriate, the pH by adding a 0.1 N solution of sodium hydroxide.

In the DOTA and calcium chloride proportions as indicated above, a calcium complex of 1,4,7,10-tetraazacyclododecane-1,4,7,10-tetraacetic acid (DOTA) and in particular predominantly a monocalcium complex of 1,4,7,10-tetraazacyclododecane-1,4,7,10-tetraacetic acid (DOTA-Ca), forms in the composition.

The density of the composition thus obtained in step c') is adjusted to a value of from 1.2010 to 1.2219 g·$cm^{-3}$ by adding water. The liquid composition is then filtered through a polyethersulfone membrane and placed in its final container, which is finally subjected to sterilization at 121° C. for 15 minutes.

Example 2

Example of a Composition in Accordance with the Invention and Results from Studies on Said Composition By virtue of the process of example 1, the following formulation is obtained:

| Ingredients | Proportions in the composition |
| --- | --- |
| Complex of formula (I) in which M represents a gadolinium ion (named complex A) | 485.1 g (0.5M) |
| DOTA | 1.011 g (2.5 mM, i.e. 0.5% mol/mol vs complex A) |
| $CaCl_2$, $2H_2O$ | 0.368 g (2.5 mM, i.e. 0.5% mol/mol vs complex A) |
| NaOH or HCl | Qs pH 5.5 ± 0.5 |
| Free gadolinium* | <1 ppm m/v |
| WFI (water for injection) | Qs 1 L |

*Measurement carried out by colorimetric method with xylenol orange

Studies of Stability Under Accelerated Conditions and of Long-Term Stability

The expression "study of stability under accelerated conditions" is intended to mean a study carried out at 40° C. over the course of six months and the expression "study of long-term stability" is intended to mean a study carried out at 25° C. over the course of 36 months (ICH conditions).

Measurements, over the course of time, of the two main entities present in the composition were carried out.

|  | T0 | | T 1 | T 3 | | T 6 | |
|---|---|---|---|---|---|---|---|
|  | Bef. s* | Aft. s** | 40° C. | 25° C. | 40° C. | 25° C. | 40° C. |
| Amount of free gadolinium (ppm m/V) | <2 | NA*** | <2 | NA*** | <1 | NA*** | NA*** |
| Amount of DOTA-Calcium complex (% mol/mol) | 0.40 | 0.18 | 0.16 | 0.23 | 0.23 | 0.20 | 0.18 |

*Bef. s = Before sterilization
**Aft. s = After sterilization
***NA = Not analyzed Free gadolinium is neither detected nor quantified in the composition. The amount of DOTA-Calcium complex decreases significantly due to the sterilization, but remains stable after six months under accelerated conditions and in the long term. Approximately half of the DOTA-Ca complex which formed in the composition after addition of the DOTA and of the calcium salt remains available in the composition to perform its free-gadolinium-trapping function.

Studies of Stability According to the Proportion of the DOTA-Ca

Several other formulations were prepared with an increasing proportion of DOTA-Ca (in particular of monocalcium complex) relative to the complex A. The concentration of free lanthanide and the concentration of DOTA-Ca were measured after the sterilization step and after three months of storage at 25° C. and 40° C.

| % mol/mol of DOTA-Ca vs complex A | | | Amount of free gadolinium (ppm m/v) | Amount of DOTA-Ca complex (% mol/mol) |
|---|---|---|---|---|
| 0.01 | T0 | Aft. s* | <0.50 | ND** |
|  | T 3 | 25° C. | <0.50 | ND** |
|  | months | 40° C. | <0.50 | ND** |
| 0.25 | T0 | Aft. s* | <0.50 | 0.14 |
|  | T 3 | 25° C. | <0.50 | 0.16 |
|  | months | 40° C. | <0.50 | 0.16 |
| 0.5 | T0 | Aft. s* | <0.50 | 0.34 |
|  | T 3 | 25° C. | <0.50 | 0.33 |
|  | months | 40° C. | <0.50 | 0.30 |
| 0.75 | T0 | Aft. s* | <0.50 | 0.53 |
|  | T 3 | 25° C. | <0.50 | 0.57 |
|  | months | 40° C. | <0.50 | 0.51 |
| 5 | T0 | Aft. s* | <0.50 | 4.60 |
|  | T 3 | 25° C. | <0.50 | 4.80 |
|  | months | 40° C. | <0.50 | 4.80 |

Aft. s*: After sterilization
ND**: Not detected

For a proportion of DOTA-Ca of between 0.01% and 5% mol/mol relative to the complex A, the concentration of free $Gd^{3+}$ is less than 0.5 ppm (m/v).

The decrease in the DOTA-Ca content with time reflects a consumption of the formulation excipient. Nevertheless, for an initial proportion of DOTA-Ca of greater than or equal to 0.25% mol/mol relative to the complex A, the amount of DOTA-Ca available after three months of storage at 40° C. remains, at least, greater than more than half the amount initially introduced. This excess of formulation excipient provides an additional guarantee in terms of uptake of the gadolinium released by the complex A during the storage of the product.

Example 3

Comparison of the Production Process According to the Invention and of Prior Art Processes Results of Assaying Gadolinium in the Compositions of PCTA-Gd after Addition of a Solution of DOTA-Calcium or after Addition of DOTA then $CaCl_2$ (in Accordance with the Invention)

A stock solution of complex between the chelating ligand of formula (I') and a gadolinium ion, enriched with free gadolinium, is used.

Added to this solution is either DOTA in powder form and then $CaCl_2$ (process in accordance with the invention), or a solution of DOTA-calcium adjusted to pH 6.0 (by extrapolating from the processes described in the prior art).

| | Amount of $Gd^{3+}$ | |
|---|---|---|
| | Addition of DOTA in powder form and then $CaCl_2$ | Addition of a solution of DOTA-calcium adjusted to pH 6.0 |
| Stock solution of complex between the chelating ligand of formula (I') and a gadolinium ion, enriched with free gadolinium | 73 ppm m/v | 73 ppm m/v |
| 1 h after addition of DOTA in powder form and adjustment of pH | <1 ppm m/v | — |
| 5 minutes after the addition of DOTA-calcium | — | 3 ppm m/v |
| 1 h after the addition of DOTA-calcium | — | 3 ppm m/v |
| 1 h 30 after the addition of DOTA-calcium | — | 3 ppm m/v |
| 2 h 15 after the addition of DOTA-calcium | — | 3 ppm m/v |
| Before sterilization | <1 ppm m/v | 4 ppm m/v |
| After sterilization | <1 ppm m/v | <3 ppm m/v |

The successive addition of DOTA in powder form and then of calcium chloride $CaCl_2$ makes it possible to efficiently complex all the $Gd^{3+}$ present in the solution of complex of chelating ligand of formula (I') and gadolinium, enriched with free gadolinium. Indeed, the considerable amount of $Gd^{3+}$ in the stock solution is no longer detected one hour after addition of the DOTA.

Conversely, when a DOTA-Calcium complex previously formed is added in the form of a solution, gadolinium ions $Gd^{3+}$ persist even after having maintained the stirring for 2 h15.

The mode of addition of the DOTA-calcium therefore has an influence on the amount of $Gd^{3+}$ in solution.

Results of Assaying of the DOTA-Calcium in the PCTA-Gd Compositions after Addition of a Solution of DOTA-Calcium or after Addition of DOTA then of $CaCl_2$ (in Accordance with the Invention)

| | Amount of DOTA-Ca (as % mol/mol) | |
|---|---|---|
| | Addition of DOTA in powder form then of $CaCl_2$ | Addition of a solution of DOTA-calcium adjusted to pH 6.0 |
| After addition of DOTA in powder form and adjustment of pH | 0.27 | — |
| 1 h after the addition of DOTA-calcium | — | 0.47 |
| 1 h 30 after the addition of DOTA-calcium | — | 0.40 |
| Before sterilization | 0.25 | 0.37 |
| After sterilization | 0.25 | 0.40 |

The consumption of DOTA-Ca is greater when the DOTA is added in powder form than when it is added directly in the form of DOTA-Ca complex. When the DOTA is added in powder form, it is capable of directly complexing the $Gd^{3+}$ in solution. The $CaCl_2$ then complexes with the remaining free DOTA, thereby explaining the smaller amount of DOTA-Ca. When the addition is carried out directly in the form of DOTA-Ca complex, there has to be an exchange of gadolinium and Ca (Complex-Gd+DOTA-Ca ⇌ Complex-Ca+DOTA-Gd). The reaction is slower and it is not complete since traces of $Gd^{3+}$ are present more than 2 h after the addition of DOTA-Calcium. The consumption of DOTA-Ca is not very significant during the sterilization for the two production processes.

The invention claimed is:

1. A liquid pharmaceutical composition comprising a complex of formula (I):

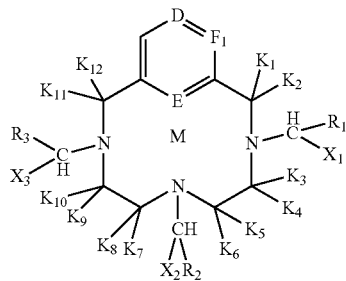

in which $R_1$, $R_2$ and $R_3$ represent —COOH, $X_1$, $X_2$ and $X_3$ represent, independently of one another, L-Y in which L represents $(CH_2)_n$ with n=1 to 3, and Y represents —$CONH_2$, —CO—$NR_7R_8$ or —$NR_7$—CO—$R_8$, in which $R_7$ represents H or a $C_1$-$C_6$ alkyl group or a $C_1$-$C_6$ hydroxyalkyl group, and $R_8$ represents a $C_1$-$C_6$ alkyl or $C_1$-$C_6$ hydroxyalkyl group, provided that at least $R_7$ or $R_8$ represents a $C_1$-$C_6$ hydroxyalkyl group;

D represents CH;
E represents N;
Fi represents CH;
$K_1$ to $K_{12}$ each independently represent H; and
M represents $Gd^{3+}$;
or an enantiomer or a diastereoisomer;
wherein said composition also comprises a calcium complex of 1,4,7,10-tetraazacyclododecane-1,4,7,10-tetraacetic acid (DOTA);
wherein M complexed with DOTA is more thermodynamically stable than M complexed in formula (I);
wherein said composition has a concentration of free paramagnetic metal of less than 1 ppm (m/v);
wherein a concentration of said complex of formula (I) comprised between 0.001 and 1.5 mol·$l^{-1}$; and
wherein a proportion of DOTA-Ca is from 0.01% to 5% mol/mol, with respect to the proportion of complex of formula (I) in said composition.

2. The composition as claimed in claim 1, characterized in that its pH is between 4.5 and 8.5.

3. The composition as claimed in claim 1, characterized in that it also comprises a buffer chosen from lactate, tartrate, malate, maleate, succinate, ascorbate, carbonate, Tris, HEPES and MES buffers and mixtures thereof.

4. The composition as claimed in claim 1, characterized in that the complex of formula (I) is chosen from the complexes of formulae:

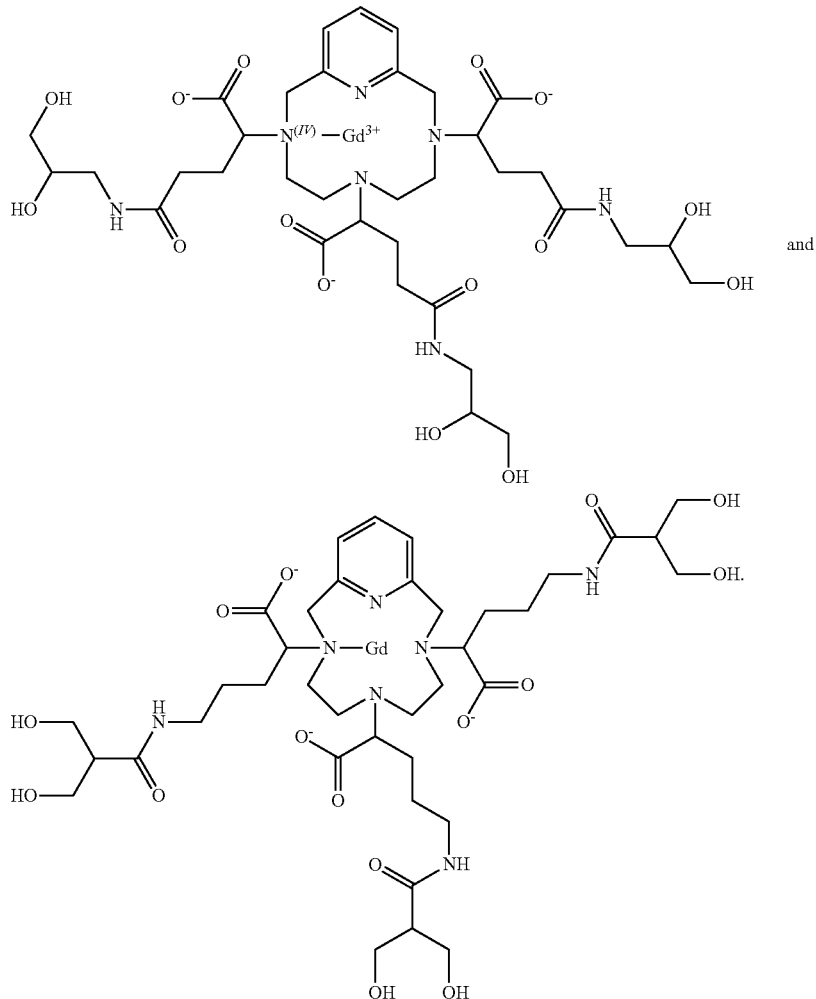

5. The composition as claimed claim 1, characterized in that it is sterile.

6. A contrast product for medical imaging, comprising the liquid pharmaceutical composition as claimed in claim 1.

7. A method for imaging the whole body or a part of the body of an individual, comprising a step of administering the composition as claimed in claim 1 to the individual and a step of obtaining one or more images of the whole body or of a part of the body of an individual by means of a medical imaging technique, in which said whole body or said part of the body of the individual comprises the composition as claimed in claim 1 and in which the image(s) is (are) associated with the complex between a chelating ligand of formula (I) as defined in claim 1 and a paramagnetic metal contained in the composition as claimed in claim 1.

8. A process for preparing a liquid pharmaceutical composition as defined in claim 1, said process comprising the following successive steps:
   a) dissolution of the complex of formula (I) as defined in claim 1, in a pharmaceutically acceptable medium,
   b) addition, to the solution obtained at the end of step a), of an amount of free DOTA comprised between 0.002% and 5% mol/mol relative to the amount of complex of formula (I) present in the composition, and
   c) addition, to the solution obtained at the end of step b), of 0.002% to 5% mol/mol of a calcium salt or of calcium oxide.

9. The process as claimed in claim 8, characterized in that it also comprises a step c') of adjustment of the pH of the solution obtained in step b) to a pH of 4.5 to 8.5.

10. The process as claimed in claim 8, characterized in that it also comprises a sterilization step.

11. A liquid pharmaceutical composition obtained according to a process comprising the following successive steps:
   a) dissolution of the complex as defined in claim 1, in a pharmaceutically acceptable medium,
   b) addition, to the solution obtained at the end of step a), of an amount of free DOTA comprised between 0.002% and 5% mol/mol relative to the amount of complex of formula (I) present in the composition, and
   c) addition, to the solution obtained at the end of step b), of 0.002% to 5% mol/mol of a calcium salt or of calcium oxide.

12. A method for imaging the whole body or a part of the body of an individual, comprising a step of administering the contrast product as claimed in claim 10 to the individual and a step of obtaining one or more images of the whole body or of a part of the body of an individual by means of a medical imaging technique, in which said whole body or said part of the body of the individual comprises the contrast product as claimed in claim 6 and in which the image(s) is (are) associated with the complex between a chelating ligand of formula (I) and a paramagnetic metal contained in the contrast product as claimed in claim 6.

13. The composition of claim 1, wherein the complex of formula (I) is a diastereoisomer selected from the group consisting of RRS, RSR, RSS and mixtures thereof.

14. The composition of claim 1, wherein the concentration of the free paramagnetic metal is less than 0.5 ppm (m/v).

15. The composition of claim 1, wherein $R_7$ represents H or a $C_1$-$C_6$ alkyl group or a $C_2$-$C_4$ hydroxyalkyl group selected from the group consisting of —$CH_2$—$CH_2OH$, —CHOH—$CH_2OH$, —CH—$(CH_2OH)_2$, —$(CH_2)_m$—$(CHOH)_p$—$CH_2OH$ with m=1 to 3, p=1 to 4 and m+p=2 to 5 and —C—$(CH_2OH)_3$.

16. The composition as claimed in claim 1, wherein $R_8$ represents a $C_1$-$C_6$ alkyl or $C_2$-$C_4$ hydroxyalkyl group selected from the group consisting of —$CH_2$—$CH_2OH$, —CHOH—$CH_2OH$, —CH—$(CH_2OH)_2$, —$(CH_2)_m$—$(CHOH)_p$—$CH_2OH$ with m=1 to 3, p=1 to 4 and m+p=2 to 5 and —C—$(CH_2OH)_3$.

17. The composition as claimed in claim 1, wherein its pH is between 5 and 6.5.

\* \* \* \* \*